United States Patent
Kawamura et al.

(10) Patent No.: US 8,097,169 B2
(45) Date of Patent: Jan. 17, 2012

(54) METHOD FOR FILTERING CHEMICAL

(75) Inventors: Yoshihisa Kawamura, Yokohama (JP);
Hisako Aoyama, Yokohama (JP); Daizo Mutoh, Yokohama (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 313 days.

(21) Appl. No.: 12/561,768

(22) Filed: Sep. 17, 2009

(65) Prior Publication Data

US 2010/0102000 A1 Apr. 29, 2010

(30) Foreign Application Priority Data

Oct. 29, 2008 (JP) ................................. 2008-278179

(51) Int. Cl.
*C02F 1/00* (2006.01)
(52) U.S. Cl. ..................................................... 210/739
(58) Field of Classification Search ........... 210/739–746
See application file for complete search history.

(56) References Cited

U.S. PATENT DOCUMENTS

| | | | | | |
|---|---|---|---|---|---|
| 4,263,805 | A | * | 4/1981 | Isley et al. | 73/38 |
| 4,304,663 | A | * | 12/1981 | Manders | 210/90 |
| 5,458,767 | A | * | 10/1995 | Stone | 210/90 |
| 5,871,651 | A | * | 2/1999 | McSpadden | 210/739 |
| 6,596,174 | B1 | * | 7/2003 | Marcus | 210/695 |
| 6,652,740 | B2 | * | 11/2003 | Schoess | 210/90 |

FOREIGN PATENT DOCUMENTS

JP 2008-72096 3/2008

* cited by examiner

*Primary Examiner* — Chester Barry
(74) *Attorney, Agent, or Firm* — Finnegan, Henderson, Farabow, Garrett & Dunner, L.L.P.

(57) ABSTRACT

A method for filtering a chemical in which a first chemical stored in a first tank is filtered by a filter and a second chemical obtained by the filtering is stored in a second tank has: adding the capture amounts corresponding to the individual first chemicals first to n-th stored in the first tank, and getting an added capture amount; and comparing the added capture amount and a predetermined limit capture amount of the filter, and exchanging the filter based on the comparison result.

20 Claims, 3 Drawing Sheets

METHOD FOR FILTERING CHEMICAL

CROSS-REFERENCE TO RELATED APPLICATION

This application is based upon and claims the benefit of priority from the prior Japanese Patent Application No. 2008-278179, filed on Oct. 29, 2008, the entire contents of which are incorporated herein by reference.

BACKGROUND OF THE INVENTION

1. Field of the Invention

The present invention relates to a method for filtering a chemical that is used in a process of manufacturing the chemical, a lithography process, and a cleaning process.

2. Background Art

In semiconductor devices according to the conventional art, a filter that filters an impurity from a used chemical may be included (for example, see Japanese Patent Laid-Open No. 2008-72096).

For example, in a filter that is used in a process of manufacturing and refining a chemical in the conventional art, a pressure of an outlet thereof is monitored, it is determined that the filter is deteriorated when the pressure is lowered, and an exchange period of time of the filter is managed based on the determination result.

Further, in another method that manages an exchange period of time of a filter, a filtering time is monitored, and it is determined that the filter is deteriorated, if a filtering time exceeds a predetermined time.

Meanwhile, a standard pore size of the filter is determined but is not constant. For this reason, even though a hole of the filter having a small pore size is clogged by a capture, a flow rate is not lowered. As a result, a deterioration of the filter may not be monitored. Further, a chemical and an impurity pass through a relatively large hole of the filter, and the amount of impurity contained in the chemical is increased.

Accordingly, if only the method for monitoring a filtering time is used, an exchange period of time of the filter cannot be properly managed.

As such, in the method for filtering a chemical according to the conventional art, a desired chemical having a standard impurity cannot be manufactured.

SUMMARY OF THE INVENTION

According to one aspect of the present invention, there is provided: a method for filtering a chemical in which a first chemical stored in a first tank is filtered by a filter and a second chemical obtained by the filtering is stored in a second tank, the method comprising:

inspecting the first chemical that is n-th (n is an integer equal to or larger than 1) stored in the first tank, and measuring a first measurement value, the first measurement value being a concentration of an impurity contained in the first chemical or an amount per unit volume of impurity contained in the first chemical;

measuring a passage liquid measure of the first chemical, which is n-th stored in the first tank, passing through the filter;

filtering the first chemical that is n-th stored in the first tank to inspect the second chemical n-th stored in the second tank, and measuring a second measurement value, the second measurement value being a concentration of an impurity contained in the second chemical or an amount per unit volume of impurity contained in the second chemical;

multiplying a value, which is obtained by subtracting the second measurement value from the first measurement value, by the passage liquid measure, and measuring a capture amount of the impurity captured by the filter, in the impurity contained in the first chemical;

adding the capture amounts corresponding to the individual first chemicals first to n-th stored in the first tank, and getting an added capture amount; and comparing the added capture amount and a predetermined limit capture amount of the filter, and exchanging the filter based on the comparison result.

According to another aspect of the present invention, there is provided: a method for filtering a chemical in which a first chemical is filtered by a filter and a second chemical obtained by the filtering, the method comprising:

inspecting the first chemical to be n-th (n is an integer equal to or larger than 1) filtered, and measuring a first measurement value, the first measurement value being a concentration of an impurity contained in the first chemical or an amount per unit volume of impurity contained in the first chemical;

measuring a passage liquid measure of the first chemical, which is n-th filtered, passing through the filter;

inspecting the second chemical that is n-th obtained by filtering the first chemical to be n-th filtered, and measuring a second measurement value, the second measurement value being a concentration of an impurity contained in the second chemical or an amount per unit volume of impurity contained in the second chemical;

multiplying a value, which is obtained by subtracting the second measurement value from the first measurement value, by the passage liquid measure, and measuring a capture amount of the impurity captured by the filter, in the impurity contained in the first chemical;

adding the capture amounts corresponding to the individual first chemicals first to n-th filtered, and getting an added capture amount; and comparing the added capture amount and a predetermined limit capture amount of the filter, and exchanging the filter based on the comparison result.

DETAILED DESCRIPTION

Hereinafter, embodiments where the present invention is applied will be described with reference to the accompanying drawings.

First Embodiment

Figure 1:
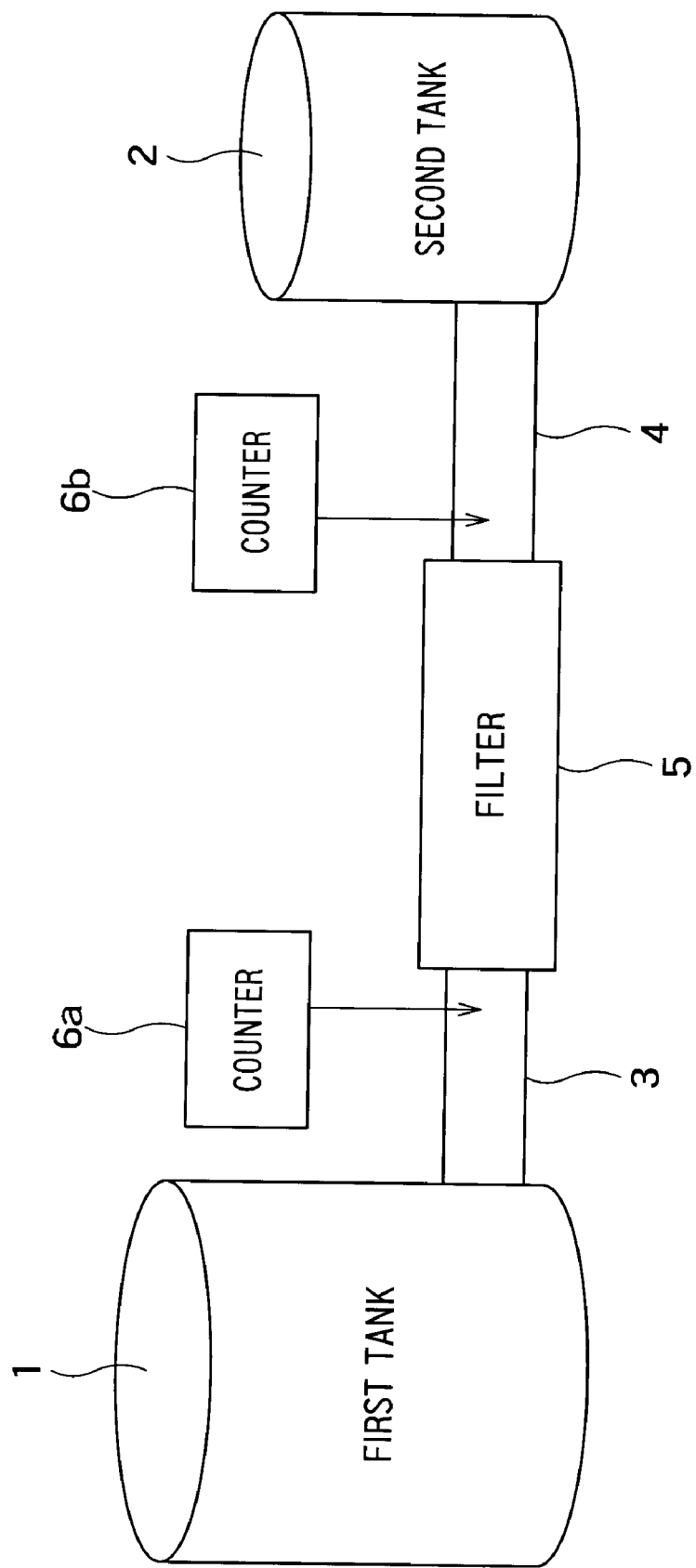
FIG. 1 is a figure showing a configuration of a process where a method for filtering a chemical according to a first embodiment of the present invention is applied.

FIG. 1 illustrates the configuration of a process where a method for filtering a chemical according to a first embodiment of the present invention is applied.

As illustrated in FIG. 1, a first tank (raw material tank) 1 and a second tank (product tank) are connected by first and second pipes 3 and 4.

In this case, it is assumed that a chemical before filtering is a first chemical (raw material) and is stored in the first tank 1. Further, it is assumed that a chemical after filtering is a second chemical (product) and is stored in a second tank 2.

Further, each of the first and second pipes 3 and 4 includes a pipe, such as a stainless used steel (SUS) pipe, a pipe subjected to electrolytic polishing, or a Teflon-coated pipe, which is selected in consideration of a property of a chemical and a desired product quality.

A filter 5 is provided between the first and second pipes 3 and 4. The filter 5 is configured to remove an impurity contained in the first chemical. For example, the impurity is a particle, a metal or an organic matter.

Further, the plurality of filters 5 may be disposed in parallel or with multi-stages.

Counters 6a and 6b are configured to measure a passage liquid measure of the first chemical of the filter 5. The counter 6a is provided in an inlet of the filter 5. Further, the counter 6b is provided in an outlet of the filter 5.

During a process of filtering the chemical having the above-described configuration, the first chemical that is stored in the first tank 1 is filtered by the filter 5, and the second chemical that is obtained by filtering is stored in the second tank 2.

In the present embodiment, after the second chemical stored in the second tank 2 is collected, the first chemical is newly stored in the first tank 1.

Next, an example of a method for filtering a chemical in the filtering process having the above-described configuration will be described.

Figure 2:
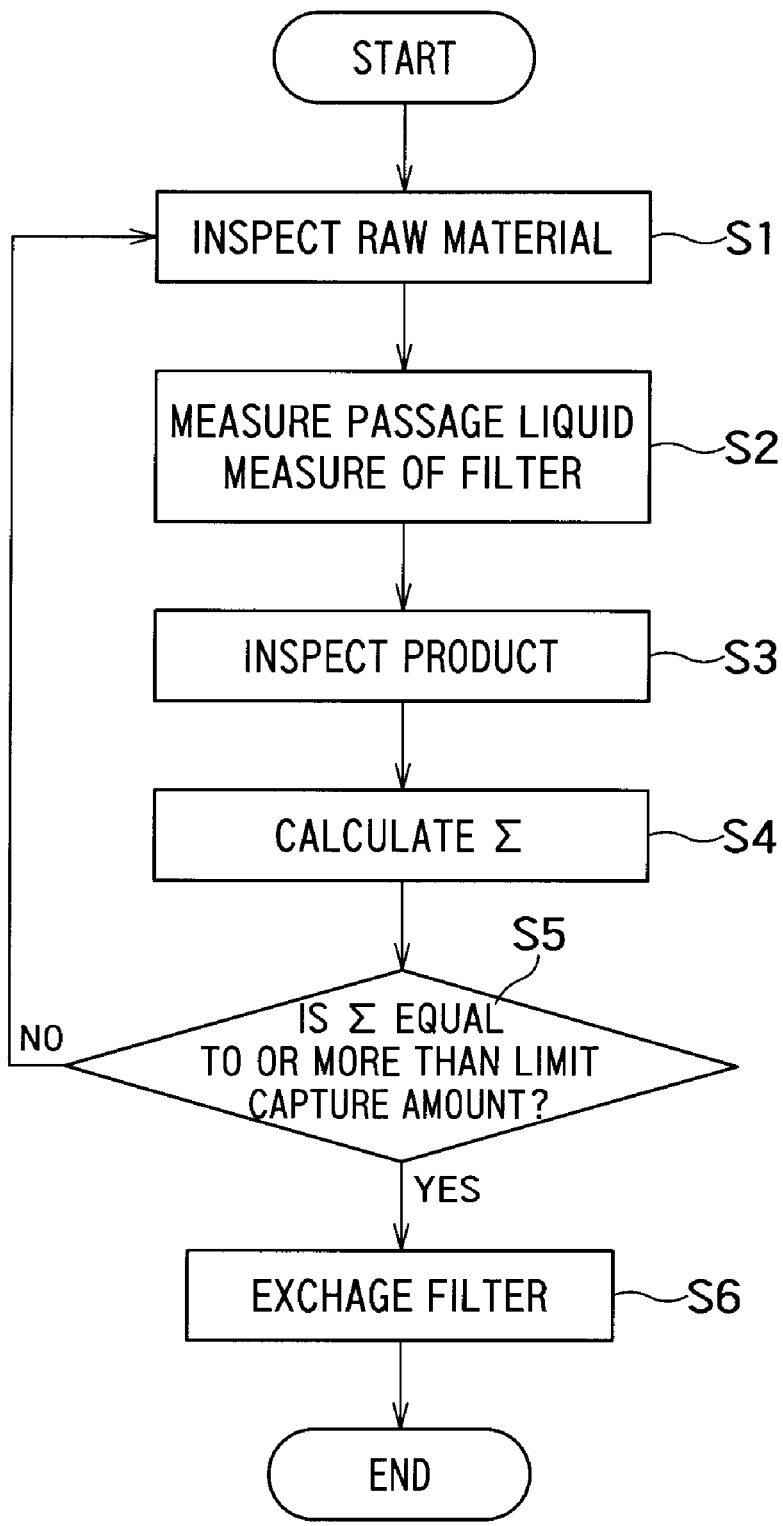
FIG. 2 is a flowchart illustrating an example of a flow of a method for filtering a chemical according to a first embodiment of the present invention.

FIG. 2 is a flowchart illustrating an example of a flow of a method for filtering a chemical according to a first embodiment of the present invention.

First, the unused (new) filter 5 is disposed in a filtering process. In addition, the first chemical that is the raw material is stored in the first tank 1. As described above, it is assumed that the first chemical is newly stored in the first tank 1 after the second chemical stored in the second tank 2 is collected.

In addition, the amount of foreign material (amount of impurity) of the first chemical (raw material) is inspected, or a concentration of a metal impurity or a concentration of an organic impurity is inspected. This inspection may be performed before the first chemical is stored in the first tank.

That is, after the unused filter 5 is disposed, the first chemical that is first stored in the first tank 1 (first filtered) is inspected, and a concentration of an impurity that is contained in the first chemical or a first measurement value $M_1 1$ that is the amount per unit volume of impurity contained in the first chemical is measured (Step S1).

Further, in a state where the first chemical is n-th (n is an integer that is equal to or larger than 1) stored in the first tank 1 after the unused filter 5 is disposed, the first chemical that is n-th stored in the first tank 1 (n-th filtered) is inspected, and a concentration of an impurity that is contained in the first chemical or a first measurement value $M_1 n$ that is the amount per unit volume of impurity contained in the first chemical is measured.

Next, after the unused filter 5 is disposed, the first chemical that is first stored in the first filter 1 is filtered by the filter 5. At this time, the counters 6a and 6b measure a passage liquid measure L1 of the first chemical, which is first stored in the first tank 1, passing through the filter 5 (Step S2).

Further, in a state where the first chemical is n-th (n is an integer that is equal to or larger than 1) stored in the first tank 1 after the unused filter 5 is disposed, the first chemical that is n-th stored in the first tank 1 is filtered by the filter 5. At this time, the counters 6a and 6b measure a passage liquid measure Ln of the first chemical, which is n-th stored in the first tank 1, passing through the filter 5.

Next, the amount of foreign material of the second chemical (product) after passing through the filter 5 is inspected, or a concentration of a metal impurity or a concentration of an organic impurity is inspected (Step S3). This inspection may be performed before the second chemical is stored in the second tank.

That is, the first chemical that is first stored in the first tank 1 is filtered and the second chemical that is first stored in the second tank 2 is inspected. Thereby, a concentration of an impurity that is contained in the second chemical or a second measurement value $M_2 1$ that is the amount per unit volume of impurity contained in the second chemical is measured.

Further, in a state where the first chemical is n-th stored in the first tank 1 after the unused filter 5 is disposed, the first chemical that is n-th stored in the first tank 1 is filtered and the second chemical that is n-th stored in the second tank 2 is inspected. Thereby, a concentration of an impurity that is contained in the second chemical or a second measurement value $M_2 n$ that is the amount of impurity per unit volume contained in the second chemical is measured.

Next, in Step S4, a value that is obtained by subtracting the second measurement value $M_2 1$ from the first measurement value $M_1 1$ is multiplied by the passage liquid measure L1, thereby obtaining a capture amount X1 of the impurity that is captured by the filter 5, in the impurity contained in the first chemical.

Further, in a state where the first chemical is n-th stored in the first tank 1 after the unused filter 5 is disposed, the value that is obtained by subtracting the second measurement value $M_2 n$ from the first measurement value $M_1 n$ is multiplied by the passage liquid measure Ln, thereby obtaining a capture amount Xn of the impurity that is captured by the filter 5, in the impurity contained in the first chemical.

In this case, the capture amount Xn of the n-th filter 5 is represented by the following Equation (1).

$$Xn=(M_1 n - M_2 n) \times Ln \qquad (1)$$

In Equation 1, as described above, $M_1 n$ indicates the n-th first measurement value, $M_2 n$ indicates the n-th second measurement value, and Ln indicates the passage liquid measure of the n-th filter 5.

Further, if the capture amounts that correspond to the individual first chemicals first to n-th stored in the first tank 1 are added, an added capture amount Σ is got (Step S4).

That is, the added capture amount Σ of the first to n-th filters 5 is represented by the following Equation 2.

$$\Sigma = X1 + X2 + \ldots + Xn \qquad (2)$$

Next, the added capture amount Σ and a predetermined limit capture amount Xlimit of the filter 5 are compared (Step S5). The limit capture amount Xlimit is determined based on absorption performance of the filter.

When the added capture amount Σ is less than the limit capture amount Xlimit, the procedure returns to Step S1, and the following raw material (first chemical that is second ((n+1)-th) stored in the first tank 1) is inspected. Thereafter, similar to the above case, the flow starting from Step S2 is carried out.

Meanwhile, when the added capture amount Σ and the limit capture amount Xlimit are compared with each other. When the added capture amount Σ is equal to or more than the limit capture amount Xlimit, the filter 5 is exchanged and the flow is completed (Step S6).

As such, the filter 5 is exchanged with a new filter, based on the comparison result between the added capture amount Σ and the predetermined limit capture amount Xlimit of the filter 5.

In comparison with the added capture amount Σ, instead of the limit capture amount Xlimit, a value obtained by subtracting the one-time capture amount from the limit capture amount Xlimit or a value obtained by multiplying the limit capture amount Xlimit by a safety coefficient α (0<α<) may be used. Thereby, the filter 5 can be securely exchanged before the capture amount of the filter 5 exceeds the limit capture amount Xlimit.

By using the flow of the method for filtering a chemical described above, an exchange period of time of the filter 5 can be properly determined.

Further, pore sizes of the filters 5, the number of filters disposed in parallel, and the number of steps can be optimized by investigating and analyzing the capture amounts in the filters. That is, optimization of the filter configuration in the manufacturing or refining process can be realized.

As described above, in the method for filtering a chemical according to the present embodiment, the filter can be properly exchanged.

In the present embodiment, the chemical that flows between the two tanks has been described. However, the present invention may be applied to any configuration where the chemical is filtered by the filter.

Second Embodiment

In a second embodiment, an example of a chemical coating device that includes a filter to filter a chemical will be described.

In the conventional art, with the development of minuteness and high precision of a semiconductor lithography process, a difference in sensitivity between material lots at the time of manufacturing a resist cannot be ignored. For example, a size of a resist pattern has been measured using a critical-dimension-measurement scanning electron microscope (CD-SEM) and a process condition (for example, exposure amount of an exposing process) of the following process has been corrected, thereby securing size precision.

However, in the above case, with respect to a variation in sensitivity for a short time due to an exchange of the resist like a difference in sensitivity between resist material lots, it is difficult to perform a correction operation according to the variation.

Accordingly, in the second embodiment, a chemical coating device that can grasp effective exchange timing of a used chemical material lot is suggested.

Figure 3:
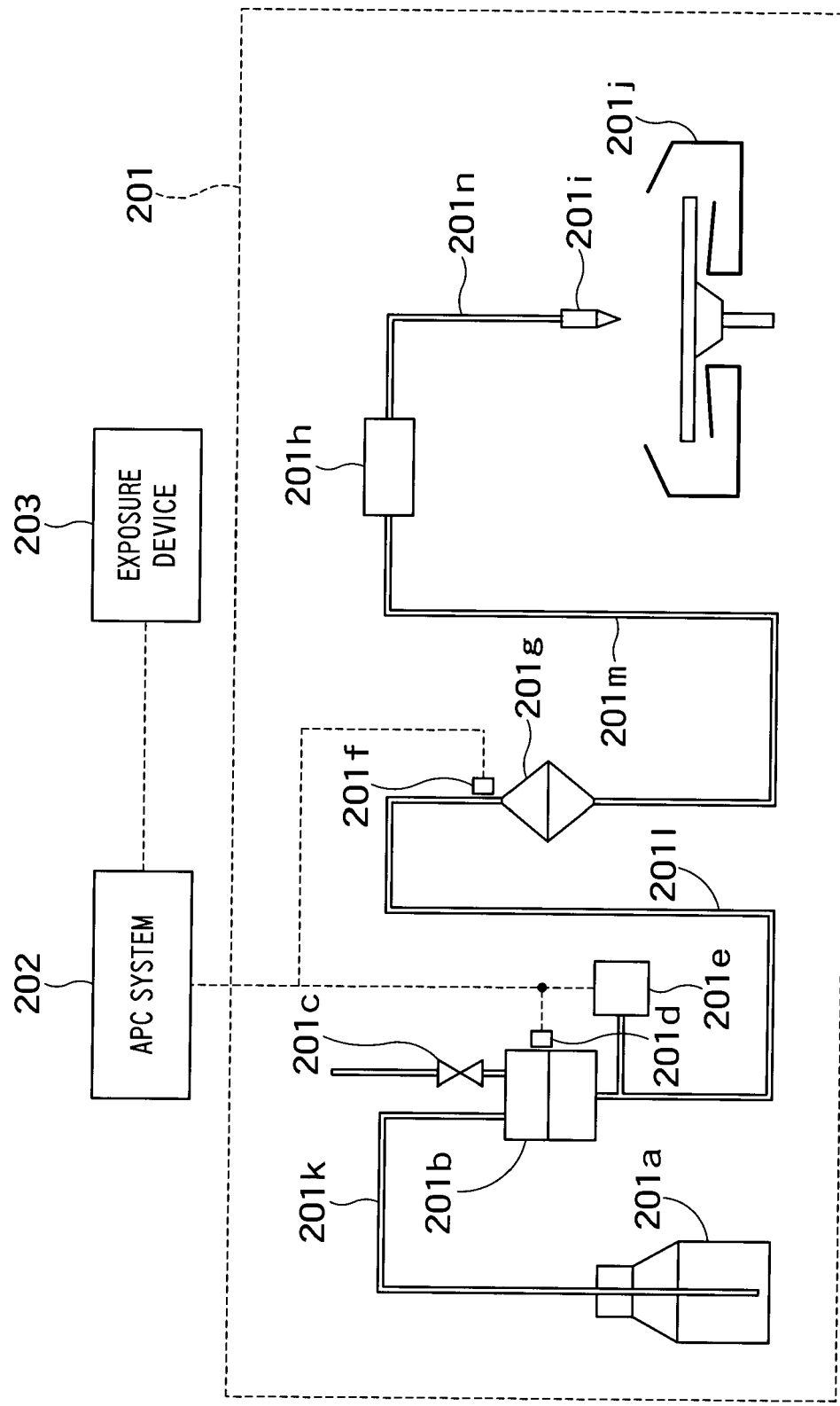
FIG. 3 is a figure illustrating an example of the configuration of a lithography process 200 including a chemical coating device 201 according to the second embodiment of the present invention.

FIG. 3 illustrates an example of the configuration of a lithography process 200 including a chemical coating device 201 according to the second embodiment of the present invention.

As shown in FIG. 3, in the lithography process 200, the chemical coating device 201, an advanced process control (APC) system 202, and an exposure device 203 are provided.

The chemical coating device 201 includes a resist bottle 201a, a sub-tank 201b, a drain valve 201c, a sub-tank liquid level sensor 201d, a monitor sample injector 201e, a detector 201f, a resist filter 201g, a tube diaphragm pump 201h, a resist nozzle 201i, a coater cup 201j, a first pipe 201k, a second pipe 201l, a third pipe 201m, and a fourth pipe 201n.

If the tube diagram pump 201h is driven, a resist chemical that is stored in the resist bottle 201a is stored in the sub-tank 201b through the first pipe 201k.

If the tube diagram pump 201h is driven, a resist chemical that is stored in the sub-tank 201b passes through the resist filter 201g through the second pipe 201l. The resist chemical that has passed through the resist filter 201g passes through the tube diaphragm pump 201h through the third pipe 201m. The resist chemical that has passed through the tube diaphragm pump 201h is supplied to the coater cup 201j through the fourth pipe 201n and the resist nozzle 201i.

In this case, the amount of resist that is contained in the sub-tank 201b is managed by the sub-tank liquid level sensor 201d. When the liquid level of the resist that is contained in the sub-tank 201b is lower than a predetermined level, the sub-tank liquid level sensor 201d is configured to activate an alarm urging an exchange of the resist bottle 201a.

The resist bottle 201a is exchanged according to the activation of the alarm. After the sub-tank liquid level sensor 201d is connected to a new resist bottle 201a, the sub-tank liquid level sensor 201d opens the drain valve 201c of the sub-tank 201b and fills a new resist chemical into the sub-tank 201b. Thereafter, the sub-tank liquid level sensor 201d starts a process by the chemical coating device 201 again.

When the amount of resist supplied to the coater cup 201j exceeds the predetermined amount after the alarm is generated, the sub-tank liquid level sensor 201d injects a monitor sample from the monitor sample injector 201e to the second pipe 201l.

In this case, the monitor sample injector 201e is disposed in the second pipe 201l near the output side of the sub-tank 201b. Further, the predetermined amount is assumed as the amount of resist that is stored in the sub-tank 201b, when the liquid level is at the predetermined level.

Further, the monitor sample has a shape of a sphere that has a diameter smaller than or equal to an inner diameter of the second pipe 201l. Further, the monitor sample is made of an opaque material (for example, polyethylene) that does not contaminate the resist chemical.

Further, the monitor sample is designed to have the same specific gravity as the resist chemical (for example, the configuration of a hollow). For this reason, the monitor sample can move in the pipe in accordance with the movement of the resist chemical.

The monitor sample and the resist chemical move in the second pipe 201l, when the resist chemical is consumed. In addition, the monitor sample is detected by the detector 201f before being supplemented to the resist filter 201g.

The detector 201f includes a light transmitting sensor using infrared rays. The detector 201f detects a passage of the opaque monitor sample in the second pipe 201l using the infrared rays. Further, light that is used to detect the monitor sample may be light having a wavelength not causing the resist chemical to be exposed, in addition to the above-described infrared rays.

Thereafter, the monitor sample is captured by the resist filter 201g.

A control circuit (not illustrated) recognizes a point of time when the amount of resist supplied to the coater cup 201j reaches the known capacity after the detector 201f detects the monitor sample as exchange timing of the resist chemical, and transmits the exchange timing to the APC system 202. Further, the control circuit is configured to grasp the amount of resist supplied to the coater cup 201j by the number of times of dispense. In this case, the known capacity is a capacity of each of the third and fourth pipes 201m and 201n and the tube diaphragm pump 201h.

In addition, the APC system 202 associates the resist bottle 201 and the process wafer with each other, and refers to performance inspection data at the time of manufacturing the resist bottle to calculate a sensitivity correction value at the time of exposing each wafer. In addition, the APC system 202 performs a control operation to correct the amount of exposure of the exposure device 203, based on the calculation result.

Thereby, resist size precision of the process wafer can be improved.

With respect to the resist chemical that is used in each process wafer, an accurate history management can be performed.

As such, according to the chemical coating device according to the present embodiment, effective exchange timing of the chemical material lot (chemical bottle) can be accurately grasped.

What is claimed is:

1. A method for filtering a chemical in which a first chemical stored in a first tank is filtered by a filter and a second chemical obtained by the filtering is stored in a second tank, the method comprising:
    inspecting the first chemical that is n-th (n is an integer equal to or larger than 1) stored in the first tank, and measuring a first measurement value, the first measurement value being a concentration of an impurity contained in the first chemical or an amount per unit volume of impurity contained in the first chemical;
    measuring a passage liquid measure of the first chemical, which is n-th stored in the first tank, passing through the filter;
    filtering the first chemical that is n-th stored in the first tank to inspect the second chemical n-th stored in the second tank, and measuring a second measurement value, the second measurement value being a concentration of an impurity contained in the second chemical or an amount per unit volume of impurity contained in the second chemical;
    multiplying a value, which is obtained by subtracting the second measurement value from the first measurement value, by the passage liquid measure, and measuring a capture amount of the impurity captured by the filter, in the impurity contained in the first chemical;
    adding the capture amounts corresponding to the individual first chemicals first to n-th stored in the first tank, and getting an added capture amount; and
    comparing the added capture amount and a predetermined limit capture amount of the filter, and exchanging the filter based on the comparison result.

2. The method according to claim 1,
    wherein, when the added capture amount is equal to or more than the limit capture amount, the filter is exchanged.

3. The method according to claim 1,
    wherein a counter that is used to measure the passage liquid measure is provided in an inlet or an outlet of the filter.

4. The method according to claim 1,
    wherein the limit capture amount is determined based on absorption performance of the filter.

5. The method according to claim 1,
    wherein the impurity is a particle, a metal or organic matter.

6. The method according to claim 2,
    wherein the impurity is a particle, a metal or organic matter.

7. The method according to claim 3,
    wherein the impurity is a particle, a metal or organic matter.

8. The method according to claim 4,
    wherein the impurity is a particle, a metal or organic matter.

9. A method for filtering a chemical in which a first chemical is filtered by a filter and a second chemical obtained by the filtering, the method comprising:
    inspecting the first chemical to be n-th (n is an integer equal to or larger than 1) filtered, and measuring a first measurement value, the first measurement value being a concentration of an impurity contained in the first chemical or an amount per unit volume of impurity contained in the first chemical;
    measuring a passage liquid measure of the first chemical, which is n-th filtered, passing through the filter;
    inspecting the second chemical that is n-th obtained by filtering the first chemical to be n-th filtered, and measuring a second measurement value, the second measurement value being a concentration of an impurity contained in the second chemical or an amount per unit volume of impurity contained in the second chemical;
    multiplying a value, which is obtained by subtracting the second measurement value from the first measurement value, by the passage liquid measure, and measuring a capture amount of the impurity captured by the filter, in the impurity contained in the first chemical;
    adding the capture amounts corresponding to the individual first chemicals first to n-th filtered, and getting an added capture amount; and
    comparing the added capture amount and a predetermined limit capture amount of the filter, and exchanging the filter based on the comparison result.

10. The method according to claim 9,
    wherein, when the added capture amount is equal to or more than the limit capture amount, the filter is exchanged.

11. The method according to claim 9,
    wherein a counter that is used to measure the passage liquid measure is provided in an inlet or an outlet of the filter.

12. The method according to claim 9,
    wherein the limit capture amount is determined based on absorption performance of the filter.

13. The method according to claim 9,
    wherein the impurity is a particle, a metal or organic matter.

14. The method according to claim 10,
    wherein the impurity is a particle, a metal or organic matter.

15. The method according to claim 11,
    wherein the impurity is a particle, a metal or organic matter.

16. The method according to claim 12,
    wherein the impurity is a particle, a metal or organic matter.

17. The method according to claim 1,
    wherein the first chemical is a resist chemical.

18. The method according to claim 2,
    wherein the first chemical is a resist chemical.

19. The method according to claim 9,
    wherein the first chemical is a resist chemical.

20. The method according to claim 10,
    wherein the first chemical is a resist chemical.

* * * * *